United States Patent [19]

Leung et al.

[11] Patent Number: 5,179,223

[45] Date of Patent: Jan. 12, 1993

[54] PROCESS FOR PRODUCING CARBAMATES FROM OXIMES

[75] Inventors: Tak W. Leung; Donald C. Best; Bernard D. Dombek, all of Charleston, W. Va.

[73] Assignee: Union Carbide Chemicals & Plastics Technology Corporation, Danbury, Conn.

[21] Appl. No.: 627,196

[22] Filed: Dec. 13, 1990

[51] Int. Cl.$^5$ ............................................. C07C 269/04
[52] U.S. Cl. ...................................... 560/33; 558/299; 560/25; 560/115; 560/158; 560/165
[58] Field of Search .................. 558/299; 560/33, 115, 560/158, 165

[56] References Cited

U.S. PATENT DOCUMENTS

| | | | |
|---|---|---|---|
| 2,041,733 | 5/1936 | Werntz et al. | 106/37 |
| 2,806,051 | 11/1955 | Brockway | 260/471 |
| 2,837,561 | 6/1958 | Beinfest et al. | 260/482 |
| 2,871,259 | 1/1958 | Levy | 260/482 |
| 3,627,813 | 12/1971 | Abbate et al. | 260/471 C |
| 4,148,819 | 4/1979 | Watts, Jr. et al. | 260/453 AL |
| 4,156,784 | 5/1979 | Dockner et al. | 560/157 |
| 4,278,805 | 7/1981 | Merger et al. | 560/25 |
| 4,336,402 | 6/1982 | Falcone et al. | 560/157 |
| 4,375,000 | 2/1983 | Merger et al. | 560/25 |
| 4,388,238 | 6/1983 | Heitkamper et al. | 260/239 E |
| 4,398,036 | 8/1983 | McCoy et al. | 560/24 |
| 4,430,505 | 2/1984 | Heitkamper et al. | 560/24 |
| 4,443,622 | 4/1984 | Smith | 560/166 |
| 4,501,915 | 2/1985 | McCoy | 560/157 |
| 4,596,678 | 6/1986 | Merger et al. | 560/344 CM |
| 4,596,679 | 6/1986 | Hellbach et al. | 560/344 |
| 4,596,744 | 6/1986 | Anderson et al. | 428/418 |
| 4,611,079 | 9/1986 | Merger et al. | 560/25 |
| 4,683,284 | 7/1987 | Goel | 528/93 |
| 4,692,503 | 9/1987 | Das et al. | 526/301 |
| 4,695,645 | 8/1987 | Merger et al. | 560/24 |
| 4,713,476 | 12/1987 | Merger et al. | 560/115 |
| 4,761,465 | 8/1988 | Speranza et al. | 528/45 |
| 4,824,925 | 4/1989 | Kamarchik, Jr. et al. | 528/45 |

FOREIGN PATENT DOCUMENTS 0059400 2/1982 European Pat. Off. .
3200559 1/1982 Fed. Rep. of Germany .
4167201 3/1969 Japan .

OTHER PUBLICATIONS

Denarie et al., *Tetrahedron Letters*, 28(47), 5823–5826 (1987).
Guise et al, Blocked Isocyanate-Terminated Prepolymers in a Delayed-Cure Durable-Press Finish for Wool. Influence of Isocyanate and Blocking Group Structure on Reactivity, Journal of Applied Polymer Science, vol. 23, 353–365 (1979).
Regulski, et al, Isocyanatoethyl Methacrylate II: The Blocked Isocyanate Derivatives, Preparation and Blocking, Dow Chemical Company (1981).
Wicks, Jr., New Developments in the Field of Blocked Isocyanates, Progress in Organic Coatings, pp. 3–28, (1981).
Potter, et al, Blocked Isocyanates In Coatings, Mobay Chemical Corporation, Pittsburgh, PA 15205 (1981).

*Primary Examiner*—José G. Dees
*Assistant Examiner*—B. Frazier
*Attorney, Agent, or Firm*—S. H. Hegedus

[57] ABSTRACT

A process for producing a carbamate is disclosed. In one embodiment, the process comprises contacting a mixture comprising a primary amine component, an urea component and a hydroxy nitrogen component, in particular at least one oxime, at conditions effective to form a carbamate. Certain novel carbamates are also disclosed.

25 Claims, No Drawings

PROCESS FOR PRODUCING CARBAMATES FROM OXIMES

BACKGROUND OF THE INVENTION

This invention relates to the production of carbamates from a unique combination of materials. More particularly, the invention relates to the production of carbamates from a mixture of reactants, including an oxime.

Carbamates, or urethanes, are useful, for example, in producing isocyanates. Many methods for the production of various carbamates have been disclosed. For example, a primary amine, urea and an alcohol can be reacted to form a carbamate and by-product ammonia. The resulting carbamate can then be thermally decomposed to form the isocyanate.

Isocyanates can be "blocked" by reaction with a material which prevents the isocyanate from reacting at room temperature with compounds that conventionally react with isocyanates, but which allows such isocyanate reaction to occur at a higher temperature. After the isocyanate is formed, it is reacted with the blocking agent to form the blocked isocyanate. The use of such blocked isocyanates is important, for example, in various coating applications. Oximes have been widely reported as effective isocyanate blocking agents. See, for example, "New Developments in the Field of Blocked Isocyanates", by Z. W. Wicks, Jr., Progress in Organic Coatings, 9 pp 3-28, (1981). Isocyanates blocked with such oximes are carbamates, e.g., oxime carbamates.

It would be advantageous to provide a new method for producing such carbamates which does not require the formation of an isocyanate as an intermediate.

SUMMARY OF THE INVENTION

New processes for producing carbamates or isocyanates blocked with oximes have been discovered. The present processes are relatively straight forward and often involve only a single reaction step. This is in contrast to prior art processes in which the isocyanate is produced first and then is reacted with the oxime to form the blocked isocyanate. In addition, the present processes can be adapted to effectively and economically produce isocyanates which are unblocked.

In one broad aspect, the present process for producing a carbamate or blocked isocyanate comprises contacting a mixture comprising a first reactant and a second reactant, and optionally a third reactant, at conditions effective to form a carbamate or blocked isocyanate. The first reactant is selected from primary amine components, urea components, N-monosubstituted urea components, N′,N-disubstituted urea components, allophanate components, oxime substituted allophanate components and mixtures thereof. The second reactant is selected from oximes and mixtures thereof. In the event the first reactant includes at least one primary amine component and/or at least one N′,N-disubstituted urea component, then the reaction mixture includes a third reactant selected from urea components, unsubstituted urethane components and mixtures thereof. Such conditions are often further effective to form ammonia and/or alcohol. If ammonia is formed, it is preferably at least partially removed during the contacting, e.g., to facilitate the formation of the carbamate.

In one embodiment, the carbamate, produced as described herein, can be decomposed, e.g., by the application of heat and/or at elevated temperature, to form the corresponding isocyanate and an oxime, in particular the oxime used to form the carbamate. Such isocyanate is useful, e.g., in the production of polyurethanes, while the oxime component from the carbamate decomposition can be recovered and recycled for use in making additional carbamate.

In addition, a new class of carbamates has been discovered. These carbamates have one of the following formulae:

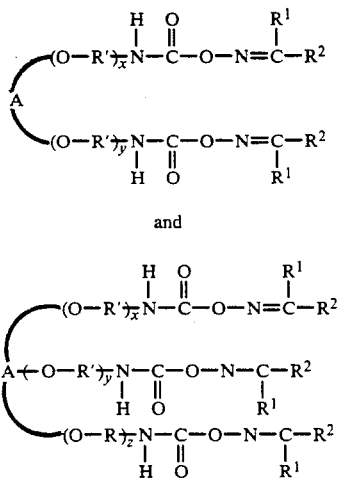

wherein each R′, $R^1$ and $R^2$ is independently selected from hydrocarbyl groups and substituted hydrocarbyl groups; each x, y and z is independently selected from integers having an average value in the range of 0 to about 1000, preferably in the range of 0 to 150 and more preferably in the range of 0 to about 50, provided that no more than one of x, y and z has an average value of 0; and A is selected from hydrocarbyl groups and substituted hydrocarbyl groups. Such carbamates may be produced in accordance with the process described herein.

A further new class of carbamates has been discovered. These carbamates have the following formula:

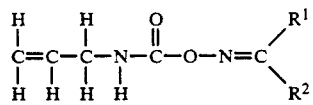

wherein $R^1$ and $R^2$ are independently selected from hydrocarbyl groups and substituted hydrocarbyl groups. Such carbamates may be produced in accordance with the process described herein.

DETAILED DESCRIPTION OF THE INVENTION

The present process provides carbamates or blocked isocyanates from a first reactant and a second reactant, and optionally a third reactant, as described herein. The second reactant is selected from oximes and mixtures thereof.

The oximes useful in the present invention are preferably selected from oximes having the ability to effectively block, i.e., as described above, the isocyanate derivable from the thermal decomposition of the carbamate formed or produced.

Preferably, the presently useful oximes have the following formula

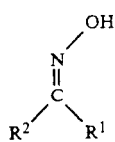

wherein $R^1$ and $R^2$ are each independently selected from hydrocarbyl groups and substituted hydrocarbyl groups. Although any suitable hydrocarbyl and substituted hydrocarbyl groups, including aliphatic groups, cycloaliphatic groups, aromatic groups and their substituted counterpart groups, may be employed, it is preferred that the $R^1$ and $R^2$ be independently selected from those groups having 1 to about 12 carbon atoms. For example, $R^1$ and $R^2$ may be independently selected from alkyl groups, such as methyl, ethyl, propyl, butyl hexyl, octyl, decyl, dodecyl and the like; substituted alkyl groups, such as the above-noted alkyl groups substituted with one or more substituent groups including elements such as oxygen, nitrogen, carbon, hydrogen, halogen, sulfur, phosphorus and the like and mixtures or combinations thereof; aryl groups, such as phenyl, naphthyl and the like; substituted aryl groups, such as the above-noted aryl groups substituted with one or more of the above-noted substituent groups and the like and mixtures or combinations thereof; aralkyl groups, such as phenyl methyl, phenyl ethyl, phenyl butyl, phenyl octyl, phenyl dodecyl and the like; substituted aralkyl groups, such as the above-noted aralkyl groups substituted with one or more of the above-noted substituent groups and the like and mixtures or combinations thereof; alkaryl groups such as methyl phenyl, ethyl phenyl, butyl phenyl, octyl phenyl, dodecyl phenyl and the like; and substituted alkaryl groups, such as the above-noted alkaryl groups substituted with one or more of the above-noted substituent groups and like and mixtures or combinations thereof.

More preferably, the total number of carbon atoms included in both $R^1$ and $R^2$ is in the range of 2 to about 9. Each of $R^1$ and $R^2$ may include a ring structure. Also $R^1$ and $R^2$ may be joined in a ring structure, for example, cycloaliphatic ring structures, aromatic ring structures, heterocyclic ring structures and their substituted counterpart ring structures. Specific examples of useful oximes include 2-butanone oxime, acetone oxime, cyclohexanone oxime, cyclopentanone oxime, acetophenone oxime, benzophenone oxime, 4-methyl-2-pentanone oxime, 5-methyl-2-hexanone oxime and mixtures thereof.

The first reactant useful in the present invention is selected from primary amine components, urea components, N-monosubstituted urea components, N', N-disubstituted urea components, allophanate components, oxime substituted allophanate components and mixtures thereof. Preferably, the first reactant is selected from primary amine components, N-monosubstituted urea components, N, N'-disubstituted urea components and mixtures thereof, especially primary amine components and mixtures thereof.

The primary amine components useful in the present invention preferably include one or more compounds having the formula

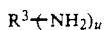

and mixtures thereof, wherein $R^3$ is selected from hydrocarbyl groups and substituted hydrocarbyl groups and u is an integer representing the number of $NH_2$ groups included in the compound. A mono-primary amine, i.e., in which the compound includes only one $NH_2$ group, may be employed, as well as polyprimary amines, i.e., in which the compound includes more than one $NH_2$ group. The number of $NH_2$ groups, and therefore the value of u, can be in the range of 1 to about 50 or about 100 or more. Preferably, u has a value in the range of 1 to about 10. In one useful embodiment, u is in the range of 1 to about 4, in particular 2 or 3.

Any suitable hydrocarbyl and substituted hydrocarbyl groups, including aliphatic groups, cycloaliphatic groups, aromatic groups, heterocyclic groups and their substituted counterpart groups, may be employed as $R^3$. In one particularly useful embodiment, $R^3$ includes 1 to about 18 carbon atoms. Exemplary $R^3$s include alkyl groups, alkenyl groups, aryl groups, alkaryl groups, alkenaryl groups, aralkyl groups, aralkenyl groups, their substituted counterpart groups and the like and mixtures thereof. Specific examples of many of these groups have been set forth previously with regard to the presently useful oximes. In addition, representative alkenyl groups include ethenyl, butenyl, octenyl, dodecenyl and the like; representative alkenylaryl groups include ethenyl phenyl, butenyl phenyl, octenyl phenyl, dodecenyl phenyl and the like; and representative arylalkenyl groups include phenyl ethenyl, phenyl butenyl, phenyl octenyl, phenyl dodecenyl and the like. Substituted alkenyl, aralkenyl and alkenaryl groups which may be employed as $R^3$ include such hydrocarbyl groups substituted with one or more substituent groups including elements such as oxygen, nitrogen, hydrogen, halogen, sulfur, phosphorus and the like and mixtures or combinations thereof.

Specific examples of suitable primary amines include: methylamine; ethylamine; propylamine; isopropylamine; allylamine; butylamine; i-butylamine; t-butylamine; hexylamine; dodecylamine; 2-ethyl-hexylamine;-tetradecylamine; hexadecylamine; octadecylamine; allylamine; 1,4-diaminobutane; 1,6-diaminohexane; 2,5-dimethyl-2,5-hexane diamine; trimethyl hexamethylene diamine; 2-methoxy-ethylamine; 3-ethoxypropylamine; 3-butoxy-propylamine; 1,4-butane diol-bis-(3-aminopropyl ether); 3-amino-propanoic acid-2-methyl propyl ester; 6-aminohexanitrile; lysine ester; 1,1-aminoundecanoic acid ester; cyclohexylamine; trimethyl cyclohexylamine; 2-norbornyl-methylamine; aniline; o-, m-, p-chloroaniline; 2,3-2,4-, 2,5-, 2,6-dichloroaniline; 3,4-dichloroaniline; p-o-nitroaniline; m-, o-, p-tolylamine; 3-trifluoromethylaniline; 3-chloro-4-methylaniline; benzylamine; phenyl-cyclohexylamine; naphthylamine; 1,4-diaminocyclohexane; 2,4-, 2,6-diamino-1-methyl cyclohexane; 5-amino-1-aminomethyl-1, 3, 3-trimethyl cyclohexane; 4,4'-diaminodicyclohexylmethane; 4,4'-diamino-3,3'-dimethyldicyclohexylmethane; 1,3-diaminobenzene; 1,4-diaminobenzene; 2-chloro-1,4-diaminobenzene, 2,4-diaminotoluene; 2,6-diaminotoluene (and mixtures with 2,4-); 2-(N-ethylamine)-4-aminotoluene; 1,3-diamino-2-methylbenzene; 1,3-bis-aminomethylbenzene; 1,3-bis-aminoethyl-4,6-dimethylbenzene; 1,3-diamino-2,4,6-triisopropylbenzene; 1,5-diaminoaphthalene; 2,7-diaminoaphthalene; benzidine;

3,3'-dichlorobenzidine; 4,4'-diaminodiphenylmethane (and crude products); 3,3'-dichlor-4,4'-diaminodiphenylmethane; 2,2,-bis-(4-aminophenyl)-propane; 1,1-bis-(4-amino phenyl)-cyclohexane; 1,1-bis-(4-amino-3-methyl phenyl)-cyclohexane; 4,4',4''-triaminotriphenylmethane, 4,4'-diaminodiphenylethers, 4,4',4''-triaminotriphenyl thiophosphate; p-methoxyaniline; p-ethoxyaniline; 1-(4-chlorphenoxy)-4-aminobenzene; 2,4-diaminodiphenylether; m-aminobenzoic acid esters, p-aminobenzoic acid ester; 3,5-diamino-2-methyl diphenylmethane; 3,5-diamino-4-methyl diphenylmethane (and mixtures thereof); 3,5-diamino-4-methyl dicyclohexylmethane; 3,5-diamino-2-methyl dicyclohexylmethane (and mixtures); 3,5,4'-triamino-4-methyl diphenylmethane; 3,5,4'-triamino-2-methyl dipheylmethane; 3,5,2'-triamino-2-methyl diphenylmethane; 3,5,2'-triamino-2-methyl diphenylmethane (and mixtures); 3,5,4'-triamino-4-methyl dicyclohexylmethane; 3,5,4'-triamino-2 methyl dicyclohexylmethane; 3,5,2'triamino-2-methyl dicyclohexylmethane (and mixtures); dibenzofuran amine; 1-aziridine propane amine; 4-pyridine methane amine; 2-pyridine amine; 1-(3-amino phenyl)-3-methyl-5-pyrazolone; pyrimidine amine; N-amino-morpholine and 2-aminobenzthiazole.

Particularly preferred amines include: propylamine; isopropylamine; allylamine; n-butylamine; sec-butylamine; t-butylamine; atacrylaine; hexamethylene diamine; cyclohexylaine; 3,3,5-methyl-5-aminomethyl cyclohexylamine; 4,4'-diamino-dicyclohexylmethane; aniline; p-chloroanile;3,4-dichloroaniline; m-tolylamine; p-methoxy aniline; 2,4-diaminotoluene; 2,6-diaminotoluene; 4,4'-diaminodiphenylmethane; 2,4'-diaminodiphenylmethane or technical mixtures of the above mentioned diaminotoluenes and diaminodiphenylmethanes.

A particularly useful class of primary amines are those selected from

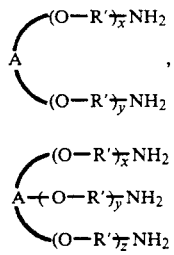

wherein each R' is independently selected from hydrocarbyl groups and substituted hydrocarbyl groups; each x, y and z is independently selected from integers having an average value in the range of 0 to about 1000, preferably in the range of 0 to about 150 and more preferably in the range of 0 to about 50 provided that no more than one of x, y and z is 0, and A is selected from hydrocarbyl groups and substituted hydrocarbyl groups. Each R' is preferably independently selected from alkyl groups, more preferably from alkyl groups having 1 to 3 carbon atoms, and still more preferably from ethyl and isopropyl. These amines can be produced using conventional procedures, such as, for example, reacting a polyalkanediol, e.g., polybutanediol, with sufficient alkylene oxide, e.g., propylene oxide, to form an adduct which is then reacted with ammonia or ammonium hydroxide in the presence of a suitable reductive amination catalyst to produce the desired amine. One such procedure is described in Watts, Jr. et al U.S. Pat. No. 4,148,819, which is incorporated herein in its entirety by reference.

These amines may often be referred to as polyoxyalkylene amines, e.g., diamines and triamines. A number of such amines are sold by Texaco Chemical Co. under the trademark JEFFAMINE ®.

For example, amines sold as JEFFAMINE ® D-series products have the formula:

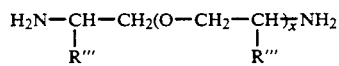

wherein each R''' is independently selected from hydrogen and methyl, and x is an integer having an average value of about 1 to about 60.

Representative polyoxypropylene diamines having the above-noted diamine structure with y equal to zero are as follows:

| | |
|---|---|
| JEFFAMINE ® D-230, | x = 2–3 |
| JEFFAMINE ® D-400, | x = 5–6 |
| JEFFAMINE ® D-2000, | x = about 33 |
| JEFFAMINE ® D-4000, | x = about 60 |

Representative polyoxypropylene triamines which are useful in the present invention and have the above-noted triamine structure are as follows:

| | |
|---|---|
| JEFFAMINE ® T-403, | Average molecular weight = 440, A derived from trimethylolpropane |
| JEFFAMINE ® T-3000, | Average molecular weight = 3000, A derived from glycerine |
| JEFFAMINE ® T-5000, | Average molecular weight = 5000, A derived from glycerine |

The urea component useful in the present invention is preferably selected from urea, polyurets and mixtures thereof. Particularly useful polyurets include biuret, triuret, tetrauret and mixtures thereof. More preferably, the urea component is selected from urea, biuret and mixtures thereof, especially urea.

The N-monosubstituted urea components useful in the present invention preferably include compounds having the formula

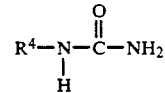

and mixtures thereof, wherein $R^4$ is selected from hydrocarbyl groups and substituted hydrocarbyl groups. The N, N'-disubstituted urea components useful in the present invention preferably include compounds having the formula

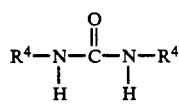

and mixtures thereof, wherein each $R^4$ is independently selected from hydrocarbyl groups and substituted hydrocarbyl groups. Preferably both $R^4$s are the same.

Exemplary $R^4$s include alkyl groups, alkenyl groups, aryl groups, alkaryl groups, alkenaryl groups, aralkyl groups, aralkenyl groups, their substituted counterpart groups and the like and mixtures thereof. Such groups preferably have up to about 20 carbon atoms. Specific examples of many of these groups have been set forth previously with regard to the presently useful oximes and primary amine components. Specific examples of suitable N-mono-and N, N'-disubstituted ureas include: N-methyl urea; N-ethyl urea; N-(n-propyl)-urea; N-(isopropyl)-urea; N-(n-butyl)-urea; N-(isobutyl)-urea; N-cyclohexyl urea; N-benzyl urea; N,N'-dimethyl urea; N,N'-diethyl urea; N,N'-di-(n-butyl)-urea; N,N'-dicyclohexyl urea; N,N'-dibenzyl urea; N,N'-di-(m-tolyl)-urea; N-phenyl urea; N,N'-diphenyl urea; and the like and mixtures thereof.

The allophanate components useful in the present invention preferably include compounds having the formula

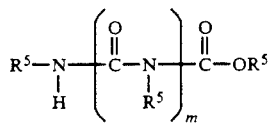

and mixtures thereof, wherein each $R^5$ is independently selected from H, hydrocarbyl groups and substituted hydrocarbyl groups, and m is an integer in the range of 1 or greater, preferably 1 to about 10, and more preferably 1. More preferably, the terminal $R^5$ bonded directly to the oxygen atom is selected from hydrocarbyl groups and substituted hydrocarbyl groups. Specific groups from which the terminal $R^5$ bonded directly to the oxygen atom can be chosen include, but are not limited to, methyl, ethyl, benzyl, propyl, iso-propyl, n-butyl, iso-butyl, sec-butyl, t-butyl, cyclohexyl, phenyl, substituted phenyl, methoxyethyl, methoxypropyl, ethoxyethyl, ethoxypropyl, propoxyethyl, propoxypropyl, butoxyethyl, butoxypropyl, phenoxyethyl, phenoxypropyl and the like, and mixtures thereof.

The oxime substituted allophanate components useful in the present invention preferably include compounds having the formula

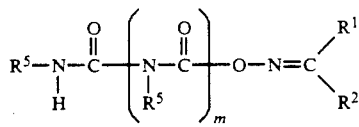

and mixtures thereof, wherein $R^1$ and $R^2$ are each independently selected from hydrocarbyl groups and substituted hydrocarbyl groups (as described previously with regard to the presently useful oximes), each $R^5$ is independently selected from H, hydrocarbyl groups and substituted hydrocarbyl groups and m is as described previously with regard to the allophanate components.

The unsubstituted urethane components useful in the present invention preferably include compounds having the formula

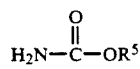

and mixtures thereof, wherein $R^5$ is selected from H, hydrocarbyl groups and substituted hydrocarbyl groups, preferably from hydrocarbyl groups and substituted hydrocarbyl groups.

Exemplary $R^5$ groups include alkyl groups, alkenyl groups, aryl groups, alkaryl groups, alkenaryl groups, aralkyl groups, aralkenyl groups, their substituted counterpart groups and the like and mixtures thereof. Such groups preferably have up to about 20 carbon atoms. Specific examples of many of these groups have been set forth previously with regard to the presently useful oximes, primary amine components, N-mono-substituted urea components, and the N, N'-disubstituted urea components. Specific examples of useful allophanates include those derived from the primary amines identified herein. Specific examples of useful oxime substituted allophanates include the above-noted allophanates which are substituted with one of the presently useful oximes (described previously) and the like and mixtures thereof. Specific examples of useful unsubstituted urethanes include methyl urethane, ethyl urethane, propyl urethane, pentyl urethane, cyclopentyl urethane, cyclohexyl urethane, hexyl urethane, methoxy ethyl urethane, ethoxyethyl urethane, propoxyethyl urethane, butoxyethyl urethane, phenoxyethyl urethane, methoxy propyl urethane, ethoxypropyl urethane, propoxypropyl urethane, butoxy propyl urethane, phenyl urethane and the like and mixtures thereof. In the event that the third reactant includes an unsubstituted urethane, the carbamate formed in the present contacting step is other than such unsubstituted urethane.

Without wishing to limit the invention to any particular theory of operation or sequence of specific chemical reactions, the following illustrates certain chemical reactions which may occur in accordance with the present invention to produce carbamates.

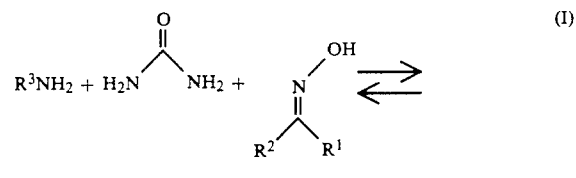

(I)

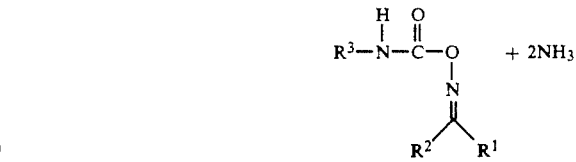

(II)

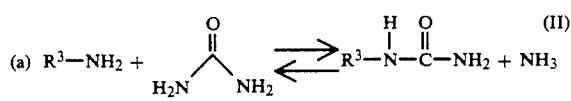

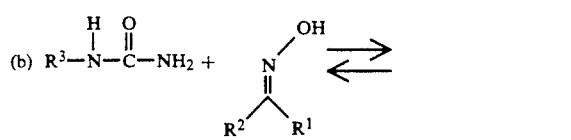

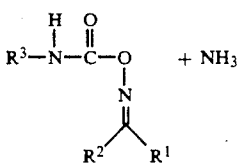

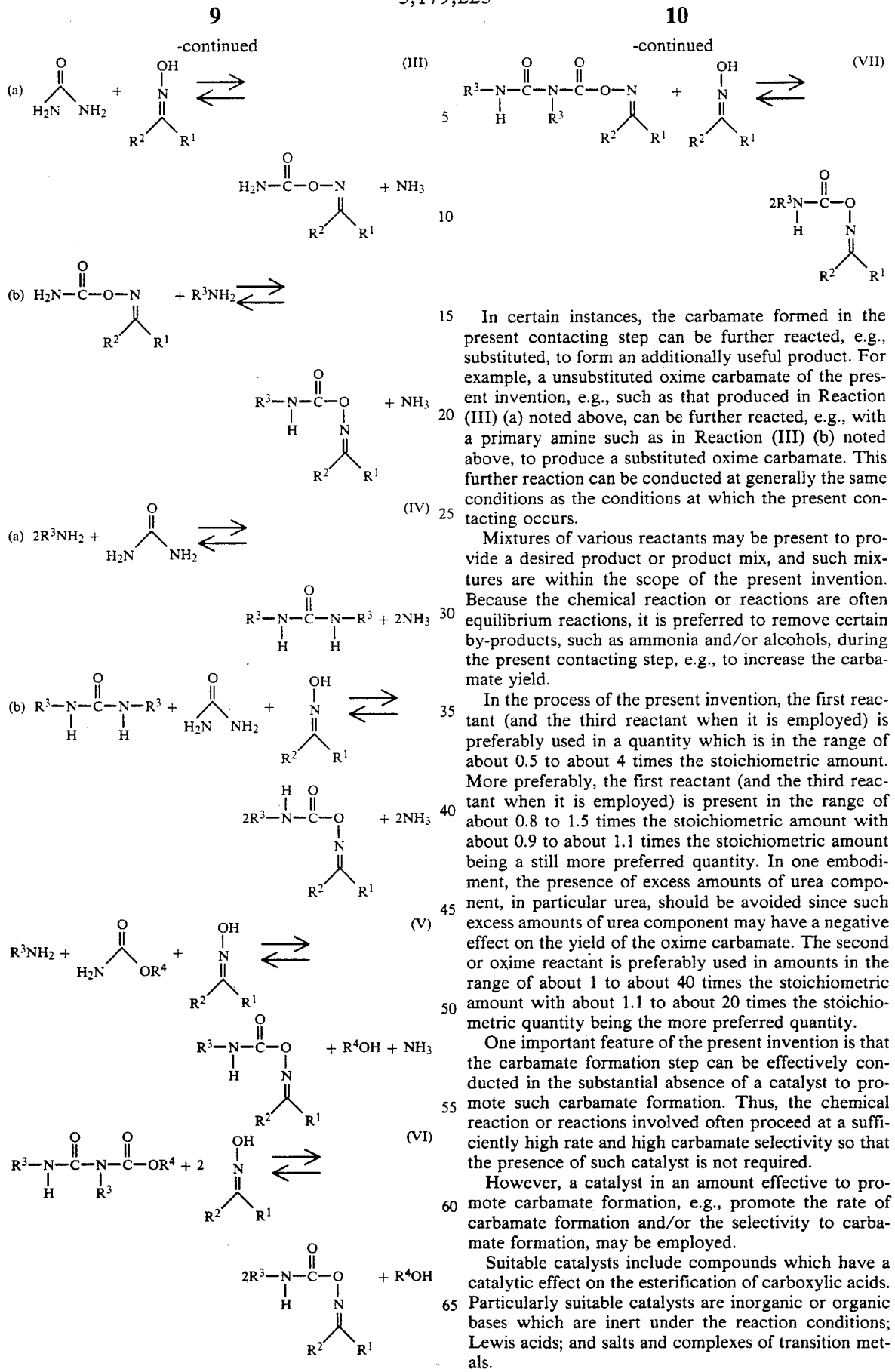

In certain instances, the carbamate formed in the present contacting step can be further reacted, e.g., substituted, to form an additionally useful product. For example, a unsubstituted oxime carbamate of the present invention, e.g., such as that produced in Reaction (III) (a) noted above, can be further reacted, e.g., with a primary amine such as in Reaction (III) (b) noted above, to produce a substituted oxime carbamate. This further reaction can be conducted at generally the same conditions as the conditions at which the present contacting occurs.

Mixtures of various reactants may be present to provide a desired product or product mix, and such mixtures are within the scope of the present invention. Because the chemical reaction or reactions are often equilibrium reactions, it is preferred to remove certain by-products, such as ammonia and/or alcohols, during the present contacting step, e.g., to increase the carbamate yield.

In the process of the present invention, the first reactant (and the third reactant when it is employed) is preferably used in a quantity which is in the range of about 0.5 to about 4 times the stoichiometric amount. More preferably, the first reactant (and the third reactant when it is employed) is present in the range of about 0.8 to 1.5 times the stoichiometric amount with about 0.9 to about 1.1 times the stoichiometric amount being a still more preferred quantity. In one embodiment, the presence of excess amounts of urea component, in particular urea, should be avoided since such excess amounts of urea component may have a negative effect on the yield of the oxime carbamate. The second or oxime reactant is preferably used in amounts in the range of about 1 to about 40 times the stoichiometric amount with about 1.1 to about 20 times the stoichiometric quantity being the more preferred quantity.

One important feature of the present invention is that the carbamate formation step can be effectively conducted in the substantial absence of a catalyst to promote such carbamate formation. Thus, the chemical reaction or reactions involved often proceed at a sufficiently high rate and high carbamate selectivity so that the presence of such catalyst is not required.

However, a catalyst in an amount effective to promote carbamate formation, e.g., promote the rate of carbamate formation and/or the selectivity to carbamate formation, may be employed.

Suitable catalysts include compounds which have a catalytic effect on the esterification of carboxylic acids. Particularly suitable catalysts are inorganic or organic bases which are inert under the reaction conditions; Lewis acids; and salts and complexes of transition metals.

Examples of suitable catalysts include: tertiary amines such as tri-n-propylamine, triethylamine, triisopentylamine, diethyl benzylamine, N,N-dimethyl benzylamine, hexahydrodimethyl aniline, N-ethyl piperazine, diethyl-(2-methoxy propyl)-amine, ethoxy morpholine, N-(2-diethyl aminoethyl)-benzamide, 4-methylimidazole, (N-(2-diethyl aminoethyl)-propionamide, 1,4-diaza-(2,2,2)-bicyclooctane, N,N-dimethyl-4-amino pyridine, 1-azabicycloheptanes, 1-azabicyclooctanes; saturated polyheterocyclic amines such as 3-methylconidine, 1-azabicyclo-(3,2,1)-octane, pyrrolizidines and quinuclidines; inorganic bases such as beryllium hydroxide and sodium, potassium, lithium, magnesium, barium or calcium hydroxide; basic alkali metal salts such as sodium carbonate, sodium sulfide, potassium carbonate and trisodium phosphate; and alkali metal salts of fatty acids or sulfonic acids.

Suitable Lewis acid catalysts include iron (II) chloride, iron (III) chloride, zinc chloride, tin (II) chloride, tin (IV) chloride, aluminum chloride, zinc cyanide, boron trifluoride and boron trifluoride etherate.

Suitable transition metal complexes useful as catalysts include cobalt, manganese and lead naphthenates; iron oleates or carbonyls; acetylacetonates of iron, nickel, cobalt, zinc, lead, aluminum, manganese, magnesium, molybdenum, titanium, thorium, zirconium and vanadium; bis-(di-benzoyl methane)-copper; bis-(ethyl acetoacetate) of copper or iron; coordination compounds of titanium, zirconium, hafnium, thorium and manganese with beta-diketones, beta-ketoesters and beta-hydroxy aldehydes; dibutyl tin dilaurate; dibutyl tin diacetate; di-(2-ethyl hexyl)-tin oxide; dioctyl tin oxide; zinc or tin salts of carboxylic acids such as zinc or tin (II) naphthanate, hexoate, calmitate, stearate or dimethyl valerate; acetates, chlorides, sulfates and octoates of divalent or trivalent cobalt, monovalent or divalent copper or divalent lead; and the like and mixtures thereof.

Particularly suitable catalysts include: 4-methylimidazole, zinc chloride, zinc acetate, zinc octoate, zinc oxide, zinc cyanide, tin (II) chloride, tin (IV) chloride, dibutyl tin dilaurate, cobalt triacetate, cobalt trichloride, cobalt trioctoate, copper (II) acetate, copper (I) chloride, copper (II) sulfate, lead acetate, lead chloride and mixtures thereof.

If a catalyst is employed, it is preferably present in an amount in the range of about 1 ppm to about 20% by weight, preferably about 100 ppm to about 5% by weight, based on the total weight of the reactants. The actual catalyst concentration employed may depend, for example, on the specific reactants being employed and on the activity of the specific catalyst used.

The present contacting step or steps are preferably carried out at temperatures in the range of about 50° C. to about 350° C., more preferably about 100° C. to about 300° C., and still more preferably about 120° C. to about 250° C.

The present contacting step or steps may be carried out under pressure or in the absence of applied pressure. The use of moderate pressures, e.g., in the range of about 1.5 atmospheres to about 10 atmospheres, may be appropriate to maintain the reactants and solvent, if any, substantially in the liquid phase. Reflux conditions may be employed during carbamate formation. Care should be exercised to avoid excessive pressures which make removal of by-product ammonia difficult to achieve while the contacting is in progress. Ammonia removal can be achieved by periodically or continuously relieving the pressure, e.g., using conventional excess pressure valves, on the reaction mixture as the contacting continues.

The present contacting step or steps can be conducted as a batch operation, a semi-batch operation or in a flow type reaction system. The type of reaction system used is not critical to the present invention, provided that carbamate is formed.

The present contacting step or steps may be carried out with or without solvents. Suitable solvents are solvents which are inert under the process conditions and which preferably have a boiling point in the range of about 50° C. to about 380° C., more preferably about 120° C. to about 250° C. Examples of suitable solvents include: n-nonane; n-butyl cyclohexane; decahydronaphthalene; n-undecane; n-dodecane; n-hexyl cyclohexane; dipentene; 1-dodecane; isopropylbenzene; 1,3-diethylbenzene; indene; n-butylbenzene; tetralin; chlorobenzene; 4-chlorotoluene; 1,2-dichlorobenzene; 2,4-dichlorotoluene; 1,2,4-trichlorobenzene; 2-chloro-4-isopropyl-1-methylbenzene; anisole; cyclohexyl ethyl ether; diethylene glycol dimethyl ether; dibenzyl ether; benzyl methyl ether; 4-methoxy toluene; para-chloroanisole; di-n-hexyl ether; phenyl-n-propyl ketone; benzophenone; acetophenone; formamide; N,N-dimethyl formamide; N,N-diethyl formamide; N-methyl formamide; dimethyl acetamide; N-methyl pyrrolidone; caprolactam; phenol substituted phenols; sulfolan; hexamethyl phosphoric acid triamide; dimethyl sulfoxide; ethylene glycol monomethyl ether acetate; di-n-propyl carbonate; cyclohexyl acetate; diisobutyl carbonate; diethylene glycol monomethyl ether acetate; diisoamyl carbonate; 2-ethyl pyridine; N,N-dimethyl-2-methylaniline; N,N-dimethylaniline; N-methyl-N-methylaniline; N,N-dimethylaniline; N-methyl-N-ethylaniline; N,N-dimethyl-2-chloroaniline; N,N-diethylaniline; quinoline; nitrocyclohexane; nitrobenzene; 2-nitrotoluene; 2,4-dimethyl-1-nitrobenzene; acetonitrile; N-capronitrile; benzonitrile; tolunitrile; diphenylether; tetramethylurea; tetrahydrofuran and phenyl acetonitrile.

To carry out the present process, the reactants, and catalyst and solvent if any, are preferably mixed and heated to the required reaction temperature.

The contacting time is preferably in the range of about 1 to about 15 hours, more preferably about 2 to about 12 hours. After or during the contacting step or steps, the carbamate-containing material may be worked up in any manner known to those in the art, such as distilling off volatile materials. It is particularly desirable that such distillation be carried out after insoluble constituents, such as insoluble catalysts, have been filtered off. In cases where the carbamate-containing material is worked up by distillation be carried out after insoluble constituents, such final fraction collected or as the distillation residue. Any of the reactants present in the end product may be separated by techniques known to those in the art. One such separation technique is taking up the distillation residue in a suitable selective solvent and subsequently filtering off the unreacted reactants.

The products obtained by the process according to the present invention represent valuable starting materials for preparing the corresponding isocyanates. Preparation of organic isocyanates from the carbamates of the present invention can be carried out by thermally splitting the carbamates into the isocyanate and the oxime component on which they are based by techniques known to those in the art. There is generally no need for the products of the present invention to be purified before they are split into an isocyanate and an oxime component.

The thermal decomposition of the present carbamates to the corresponding isocyanates is preferably conducted by contacting the carbamate or carbamates at an elevated temperature, more preferably in the range of about 80° C. to about 600° C., for a time sufficient, more preferably in the range of about 0.01 hours to about 5 hours or more, to produce the corresponding isocyanate or isocyanates and oxime component or components from which the carbamate or carbamates were derived. One or more catalysts, such as those conventionally employed to thermally decompose carbamates to isocyanates, may be employed to promote the rate of formation of and/or selectivity to the isocyanate or isocyanates. Suitable solvents may also be employed. Sub-atmospheric, atmospheric and/or super-atmospheric pressure may be employed. The product isocyanate or isocyanates can be recovered from the product mixture using conventional techniques, such as distillation, extraction, filtration and the like. The oxime component product from the carbamate decomposition is preferably recovered and more preferably is used in accordance with the process of the present invention to produce additional carbamate product.

The following non-limiting examples illustrate certain aspects of the present invention.

EXAMPLE 1

10 g (0.10 mole) of cyclohexylamine. 6.1 g (0.10 mole) of urea and 130 g (1.5 moles) of 2-butanone oxime were heated slowly to reflux at 150° C. After 4.0 hours, the reaction mixture was cooled. The reaction mixture was analyzed by high performance liquid chromatography. The yield of the oxime carbamate or 2-butanone oxime blocked cyclohexyl isocyanate was 87%.

EXAMPLE 2

20 g (0.165 mole) of alpha-methylbenzylamine, 10.0 g (0.167 mole) of urea and 200 g (2.3 moles) of 2-butanone oxime were heated slowly to reflux at 150° C. After 6.0 hours, the reaction mixture was cooled. The reaction mixture was analyzed by high performance liquid chromatography. The yield of the oxime carbamate or 2-butanone oxime blocked alpha-methylbenzyl isocyanate was 78%.

EXAMPLE 3

10.2 g (0.10 mole) of 4-methylphenylamine, 5.8 g (0.97 mole) of urea and 195 g (0.59 moles) of 4-methyl 2-pentanone oxime were heated slowly to reflux at 170° C. After 4.0 hours, the reaction mixture was cooled. The reaction mixture was analyzed by high performance liquid chromatography. The yield of the oxime carbamate or 4-methyl 2-pentanone blocked 4-methylphenyl isocyanate was 66%.

EXAMPLE 4

4.0 g (0.023 mole) of isophorone diamine, 5.3 g (0.088 mole) of urea and 87 g (0.86 moles) of 2-butanone oxime were heated slowly to reflux at 150° C. After 6.0 hours, the reaction mixture was cooled. The reaction mixture was analyzed by high performance liquid chromatography. The yield of the oxime carbamate or 2-butanone oxime blocked isophorone diisocyanate was 50%.

EXAMPLE 5

4.0 g (0.023 mole) of isophorone diamine, 5.3 g (0.088 mole) of urea and 50 g (0.39 mole) of 5-methyl-2-hexanone oxime were heated slowly to reflux at 153° C. After 6.0 hours, the reaction mixture was cooled. The reaction mixture was analyzed by infra red spectroscopy and gas chromatography techniques, which provided indications that the oxime carbamate or 5-methyl 2-hexanone oxime blocked isophorone diisocyanate had been formed.

EXAMPLE 6

5.6 g (0.033 mole) of isophorone diamine, 4.0 g (0.0.67 mole) of urea and 125 g (1.1 mole) 4-methyl-2-pentanone oxime were heated slowly to reflux at 145° C. After 3.5 hours, the reaction mixture was cooled. The yield of the oxime carbamate or 4-methyl 2-pentanone oxime blocked isophorone diisocyanate based on high performance ligand chromatography analysis was 52%.

EXAMPLE 7

3.0 g (0.018 mole) of isophorone diamine, 2.1 g (0.035 mole) of urea and 100 g (1.15 moles) of 2-butanone oxime were heated slowly to reflux at 145° C. for 2.0 hours. At this time, 0.3 g of 4-methylimidazole was added to the reaction mixture. The reaction mixture was allowed to reflux for another 2.0 hours. The reaction mixture was then cooled and analyzed by high performance liquid chromatography. The yield of the oxime carbamate or 2-butanone oxime blocked isophorone diisocyanate was 70%.

EXAMPLE 8

18 g (1.06 mole) of isophorone diamine, 13.0 g (2.2 mole) of urea and 150 g (1.5 moles) of cyclohexanone oxime were allowed to react at 180° C. The reaction was monitored by infra red spectroscopy. The formation of the oxime carbamate or cyclohexanone oxime blocked isophorone diisocyanate, was apparent by the appearance of a strong absorption of $1725 \text{ cm}^{-1}$.

EXAMPLE 9

5.7 g (0.10) of allylamine, 6.0 g (0.0.67 mole) of urea and 110 g (0.96 mole) of 4-methyl-2-pentanone oxime were heated slowly to reflux at 145° C. Allylamine which escaped the reaction mixture was trapped by a dry ice-acetone trap. After 4.0 hours, the reaction mixture was cooled. 1.4 g of allylamine was found to be trapped in the cold trap. The yield of oxime carbamate or 4-methyl 2-pentanone oxime blocked allyl isocyanate determined by high performance liquid chromatography analysis based on the allylamine reacted was 57%.

EXAMPLE 10

5.6 g (0.050 mole) of isophorone diamine, 6.1 g (0.10 mole) of urea and 120 g (1.4 mole) of 2-butanone oxime were heated slowly to reflux at 145° C. The formation of the oxime carbamate or 2-butanone oxime blocked 1,6-hexanediisocyanate was observed by infra red spectroscopy as a strong absorption of $1730 \text{ cm}^{-1}$ appeared. After 2.0 hours, the reaction mixture was cooled as a substantial amount of product precipitated out of the solution. The white precipitate was analyzed by infrared spectroscopy and was found to contain both the oxime carbamate and some polyurea.

EXAMPLE 11

200 g (0.10 mole) of an amine sold by Texaco Chemical Co. under the Trademark JEFFAMINE ® D-2000, 12.5 (0.21 mole) of urea and 200 g (2.3 moles) of 2-butanone oxime were refluxed at 145° C. for 6.0 hours. The reaction was followed by infra red spectroscopy. The formation of the oxime carbamate is evidenced by the appearance of a strong infra red absorption at 1730 cm$^{-1}$. The reaction solution was then cooled to room temperature.

EXAMPLE 12

50 g of the oxime carbamate from Example 11 was placed in a dropping funnel. The oxime carbamate was then slowly fed to the hot finger (250° C.) of a falling film evaporator under reduced pressure (10 mm Hg). 2-Butanone oxime separated from the mixture and was collected on the upper (or side) flask of the evaporator. A diisocyanate was collected on the bottom flask of the evaporator. Another batch of 50 g of the reaction mixture from Example 11 was fed this way. About 50 g of product accumulated in the bottom flask at this point. Infra-red spectroscopy showed incomplete decomposition of the oxime carbamate. Therefore, this material was returned to the dropping funnel and was fed to the hot finger three more times. After the fourth time, it was observed that the infra-red spectrum was not much different from the material after the third time passing through the hot finger. The isocyanate content based on infra-red spectroscopy is about 2.5%. Close to quantitative yield of diisocyanate was obtained based on calculation.

While this invention has been described with respect to various specific examples and embodiments, it is to be understood that the invention is not limited thereto and that it can be variously practiced within the scope of the following claims.

We claim:

1. A process for producing an oxime carbamate comprising:
contacting a mixture comprising a primary amine component, a urea component and at least one oxime at conditions effective to form an oxime carbamate.

2. The process of claim 1 wherein said contacting conditions are further effective to form ammonia, and said process further comprises removing ammonia during said contacting.

3. The process of claim 2 wherein said at least one oxime has the following formula

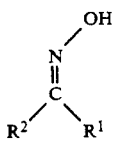

wherein R$^1$ and R$^2$ are each independently selected from the class consisting of hydrocarbyl groups and substituted hydrocarbyl groups.

4. The process of claim 3 wherein each of R$^1$ and R$^2$ has 1 to about 12 carbon atoms.

5. The process of claim 3 wherein R$^1$ and R$^2$ are joined together in a ring structure.

6. The process of claim 3 wherein R$^1$ and R$^2$ are each independently selected from the class consisting of alkyl groups, substituted alkyl groups, aryl groups, substituted aryl groups, aralkyl groups, substituted aralkyl groups, alkaryl groups and substituted alkaryl groups.

7. The process of claim 2 wherein said at least one oxime is selected from the group consisting of 2-butanone oxime, acetone oxime, cyclohexanone oxime, cyclopentanone oxime, acetophenone oxime, benzophenone oxime, 4-methyl-2-pentanone oxime, 5-methyl-2 hexanone oxime and mixtures thereof.

8. The process of claim 1 wherein said primary amine component is selected from the group consisting of mono-primary amines, poly-primary amines and mixtures thereof.

9. The process of claim 1 wherein said primary amine component is selected from compounds having the formula

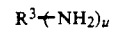

and mixtures thereof, wherein R$^3$ is selected from the class consisting of hydrocarbyl groups and substituted hydrocarbyl groups and u is an integer in the range of 1 to about 50.

10. The process of claim 9 wherein u is in the range of 1 to about 10.

11. The process of claim 9 wherein u is in the range of 1 to about 4.

12. The process of claim 1 wherein said urea component is selected from the group consisting of urea, polyurets and mixtures thereof.

13. The process of claim 1 wherein said urea component is selected from the group consisting of urea, biuret and mixtures thereof.

14. The process of claim 1 wherein said urea component is urea.

15. The process of claim 1 wherein said contacting takes place in the presence of a catalyst composition in an amount effective to promote the formation of said oxime carbamate.

16. The process of claim 1 wherein said conditions are effective to form ammonia.

17. The process of claim 16 which further comprises removing ammonia during said contacting.

18. A process for producing a oxime carbamate comprising:
contacting a mixture comprising a primary amine urea and an oxime at conditions effective to form a oxime carbamate and ammonia; and
removing ammonia during said contacting.

19. The process of claim 18 wherein said primary amine is selected from compounds having the formula

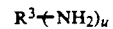

and mixtures thereof, where R$^3$ is selected from the class consisting of hydrocarbyl groups and substituted hydrocarbyl groups, and u is an integer in the range of 1 to about 10; and said oxime is selected from compounds having the formula

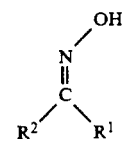

and mixtures thereof, wherein R$^1$ and R$^2$ are each independently selected from the class consisting of hydrocarbyl groups and substituted hydrocarbyl groups.

20. The process of claim 19 wherein each of $R^1$ and $R^2$ has 1 to about 12 carbon atoms.

21. The process of claim 20 wherein $R^1$ and $R^2$ are joined together in a ring structure.

22. The process of claim 20 wherein $R^1$ and $R^2$ are each independently selected from the class consisting of alkyl groups, substituted alkyl groups, aryl groups, substituted aryl groups, aralkyl groups, substituted aralkyl groups, alkaryl groups and substituted alkaryl groups.

23. The process of claim 18 wherein said oxime is selected from the group consisting of 2-butanone oxime, acetone oxime, cyclohexanone oxime, cyclopentanone oxime, acetophenone oxime, benzophenone oxime, 4-methyl-2-pentanone oxime, 5-methyl-2 hexanone oxime and mixtures thereof.

24. The process of claim 18 wherein said primary amine is selected from the group consisting of mono-primary amines, poly-primary amines and mixtures thereof.

25. The process of claim 18 wherein said contacting takes place in the presence of a catalyst composition in an amount effective to promote the formation of said oxime carbamate.

* * * * *